United States Patent
Shanks et al.

(10) Patent No.: US 8,814,924 B2
(45) Date of Patent: Aug. 26, 2014

(54) FUNGAL INFECTION THERAPY DEVICE WITH LOW LEVEL LASER

(75) Inventors: Steven C Shanks, McKinney, TX (US); Kevin B Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 40 days.

(21) Appl. No.: 13/344,257

(22) Filed: Jan. 5, 2012

(65) Prior Publication Data

US 2012/0109265 A1    May 3, 2012

Related U.S. Application Data

(63) Continuation of application No. 13/039,930, filed on Mar. 3, 2011, now abandoned.

(60) Provisional application No. 61/314,957, filed on Mar. 17, 2010.

(51) Int. Cl.
*A61N 5/06* (2006.01)
*A61N 5/067* (2006.01)
*A61B 18/20* (2006.01)

(52) U.S. Cl.
CPC ......... *A61N 5/0616* (2013.01); *A61N 2005/067* (2013.01); *A61B 2018/2085* (2013.01); *A61N 2005/0642* (2013.01); *A61N 2005/0659* (2013.01)
USPC ............. 607/89; 607/88; 606/10; 606/11

(58) Field of Classification Search
None
See application file for complete search history.

(56) References Cited

U.S. PATENT DOCUMENTS

| | | | | |
|---|---|---|---|---|
| 3,101,716 A | * | 8/1963 | Cornell, Jr. | 607/91 |
| 5,046,494 A | | 9/1991 | Searfoss et al. | |
| 5,466,248 A | * | 11/1995 | Whitson-Newman | 607/88 |
| 5,947,956 A | * | 9/1999 | Karell | 606/9 |
| 6,035,545 A | * | 3/2000 | Jones | 34/202 |
| 6,761,730 B1 | * | 7/2004 | Johnson et al. | 607/94 |
| 6,776,790 B1 | * | 8/2004 | Maruyama et al. | 607/94 |
| 6,899,724 B1 | * | 5/2005 | Johnson et al. | 607/94 |
| 7,118,588 B2 | | 10/2006 | Tucek et al. | |

(Continued)

FOREIGN PATENT DOCUMENTS

JP       2003174922       6/2003

OTHER PUBLICATIONS

International Search Report, International Application No. PCT/US2011/028729, Korean Intellectual Property Office, Nov. 25, 2011.

(Continued)

*Primary Examiner* — Lynsey Crandall
(74) *Attorney, Agent, or Firm* — Etherton Law Group, LLC

(57) ABSTRACT

A portable, small-footprint laser device contains one or more housings in which a laser energy source and an optical arrangement are disposed. The housing produces a laser beam spot that may be rotated and scanned to apply laser energy to a target area. The laser device receives treatment parameters and uses them to program a treatment regimen in which activation and movement of the housings is automated. The laser device may be used to apply a treatment regimen to a patient's hands or feet that are infected by Onychomycosis. In the treatment regimen, certain wavelengths of laser energy are applied at a predetermined duration. The treatment may be repeated, and a topical anti-fungal medication may be applied to aid in the efficacy of the treatment.

3 Claims, 13 Drawing Sheets

(56) References Cited

U.S. PATENT DOCUMENTS

| | | |
|---|---|---|
| 2002/0111656 A1 | 8/2002 | Lach |
| 2003/0088297 A1* | 5/2003 | Stoppler ............... 607/94 |
| 2003/0109860 A1 | 6/2003 | Black |
| 2003/0153962 A1* | 8/2003 | Cumbie ............... 607/94 |
| 2004/0162549 A1 | 8/2004 | Altshuler |
| 2004/0210214 A1 | 10/2004 | Knowlton |
| 2005/0197681 A1 | 9/2005 | Barolet |
| 2005/0203594 A1 | 9/2005 | Lim et al. |
| 2006/0009823 A1 | 1/2006 | Richardson |
| 2006/0212098 A1* | 9/2006 | Demetriou et al. ........ 607/86 |
| 2006/0224218 A1* | 10/2006 | Tucek et al. ............ 607/89 |
| 2008/0058905 A1* | 3/2008 | Wagner ................ 607/88 |
| 2008/0234786 A1 | 9/2008 | Cumbie |
| 2009/0143842 A1* | 6/2009 | Cumbie et al. ........... 607/88 |
| 2009/0171266 A1 | 7/2009 | Harris |

OTHER PUBLICATIONS

Written Opinion of the International Searching Authority, International Application No. PCT/US2011/028729, Korean Intellectual Property Office, Nov. 25, 2011.

* cited by examiner

FUNGAL INFECTION THERAPY DEVICE WITH LOW LEVEL LASER

CROSS-REFERENCE TO RELATED APPLICATIONS

This application claims the benefit and is a continuation of co-pending U.S. patent application Ser. No. 13/039,930 filed Mar. 3, 2011, which is a non-provisional application of U.S. Provisional Pat. App. Ser. No. 61/314,957, filed Mar. 17, 2010.

FIELD OF INVENTION

This invention relates generally to therapies with a laser device. More particularly, this invention relates to methods and devices for treating a fungal infection with low level laser energy.

BACKGROUND

Onychomycosis ("OM") is a fungal infection of toenails or fingernails. The infection may encompass any component of the nail, including the nail bed, nail plate, or nail matrix. OM can become very unsightly and may produce pain, discomfort, and disfigurement, all of which can lead to physical and occupational limitations. A disorder such as OM may have a detrimental effect on an individual's quality of life, affecting his psychosocial and emotional well-being. The main subtypes of OM are distal lateral subungual OM ("DLSO"), white superficial OM ("WSO"), proximal subungual OM ("PSO"), endonyx OM ("EO"), and candidal OM. Patients may have a combination of these subtypes. Total dystrophic OM refers to the most advanced form of any subtype. The onset of fungal infection is caused by three main classes of fungi: dermatophytes, yeasts, and nondermatophyte molds. The most common cause of OM worldwide is due to the infection of dermatophytes, including the genera *Epidermophyton, Microsporum*, and *Trichophyton*. There are two major pathogens that account for a majority of OM cases, *Trichophyton rubrum* and *Trichophyton mentagrophytes*.

There are several treatment options for clinicians, including systemic or topical antifungal medications and natural remedies. However, the rate of success remains low, the rate of recurrence remains high, and the costs and risks involved may be steep for some patients. For example, the most effective accepted treatments are prescription oral pharmaceuticals that have significant negative side effects, such as skin rash and liver damage. An effective alternative to pharmacological solutions is needed that is safe for the patient and prevents recurrence of the infection.

Low level laser therapy ("LLLT") is used in the treatment of a broad range of conditions. LLLT improves wound healing, reduces edema, and relieves pain of various etiologies, including successful application to wound and surgical sites to reduce inflammation and pain. LLLT is also used in the treatment and repair of injured muscles and tendons. LLLT utilizes low level laser energy, wherein the treatment has a dose rate that causes no immediate detectable temperature rise of the treated tissue and no macroscopically visible changes in tissue structure. Consequently, the treated and surrounding tissue is not heated or damaged, and the patient feels no sensation during treatment. Some LLLT applications have effectively photodestroyed a targeted biological element under suitable treatment conditions. For example, LLLT may be used in fat reduction to create a transition pore in fat cell walls, through which fat is released into the interstitial space.

There are a number of variables in laser therapy, including the wavelength of the laser beam, the area impinged by the laser beam, the shape of the beam spot when it impinges the area, the power of the laser source, the intensity or fluence of the laser energy, the laser pulse width, and the treatment duration. These variables typically depend heavily on the tissue characteristics of the specific patient, and the success of each therapy depends on the relationship and combination of these variables. For example, fat reduction may be facilitated with one regimen utilizing a given power, wavelength, and treatment duration, whereas pain may be treated with a regimen utilizing a different wavelength and treatment duration, and inflammation a third regimen. Specific devices may be used for each type of therapy.

Therefore, an object of this invention is to provide laser therapy devices and methods of using the devices to treat OM and other fungal infections of the fingernails or toenails. A further object of the invention is to incite photodestruction of fungal bacteria without adversely affecting surrounding healthy tissue. It is another object of this invention to destroy fungal bacteria using laser light in multiple different pulse widths. It is a particular object of this invention to provide methods of using a compact, standalone laser device to provide low level laser therapy which can be used to treat OM and other fungal infections. It is another particular object of this invention to provide methods of using a hand-held therapeutic laser device to provide low level laser therapy which can be used to treat OM and other fungal infections.

SUMMARY OF THE INVENTION

This invention is a method of treating OM using a laser device that can simultaneously emit one or more wavelengths of laser light. The device enables laser light of one or more pulse widths, one or more beam shapes, and one or more spot sizes to be applied externally to the affected area of a patient's body. The laser light may be continuous or pulsed. The device may include multiple laser sources. In the preferred embodiment, two semiconductor diode laser sources simultaneously provide two separate laser beams, one laser beam producing red laser light and the other producing violet laser light. Most preferably, the laser sources are contained in a portable, compact, free-standing laser device into which the patient places the infected hand or foot.

The laser device is activated and laser energy is scanned across the infected area of the patient's first hand or foot. The laser energy source may be nearly touching the skin or held at a distance of up to about 10 inches, or further, from the nail surface. The laser energy may be applied for a duration of about 10 minutes to about 30 minutes on the patient's first hand or foot. The application may be repeated on another infected appendage if desired. The entire treatment may be repeated after the first application. Following the second treatment, the patient may apply a topical anti-fungal medication for 12 weeks to prevent re-infection.

BRIEF DESCRIPTION OF THE DRAWINGS

FIG. 8b is a front perspective view of the scanner assembly of the laser device of FIG. 8a.

FIG. 9 is a front right perspective view of the laser device of FIG. 8a.

DETAILED DESCRIPTION OF THE INVENTION

Figure 1:
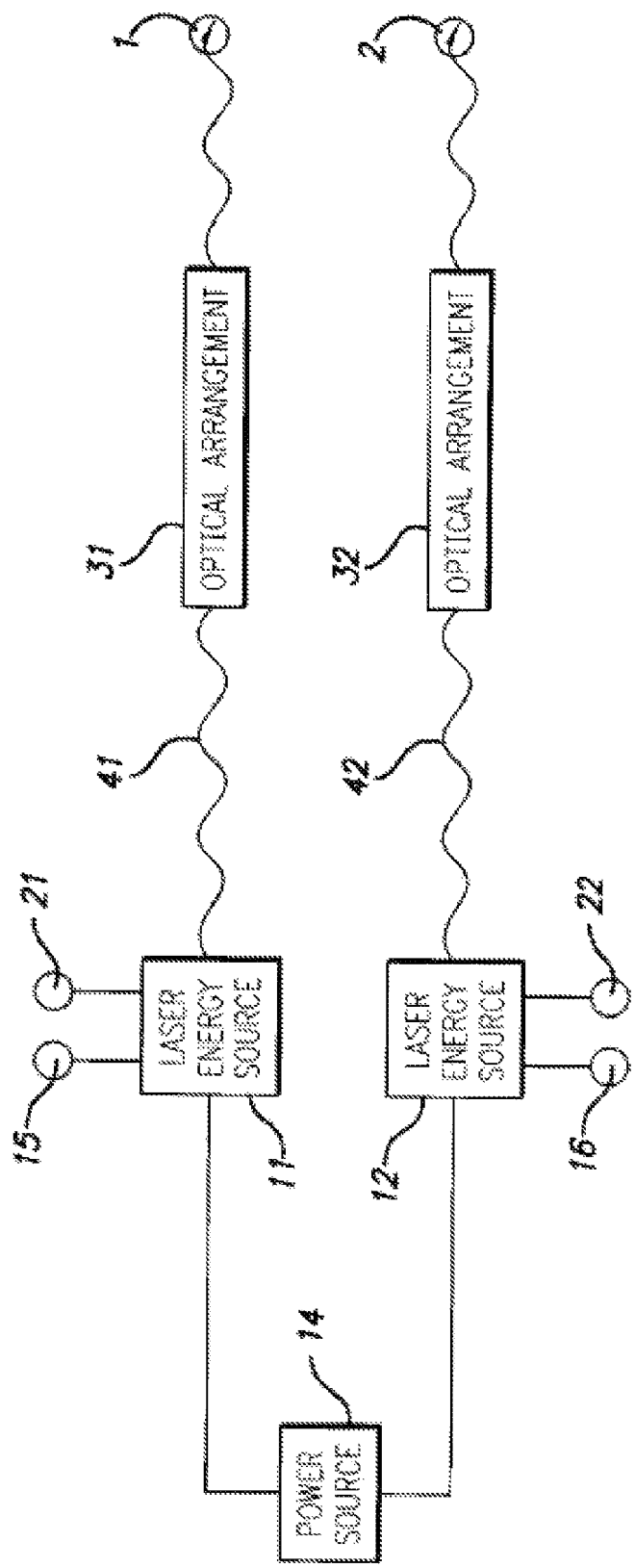
FIG. 1 is an electrical and electromagnetic schematic illustration of the preferred embodiment of the present invention.

Referring to the drawings, there are illustrated a plurality of laser devices that may be used to perform the inventive methods herein, which are methods for treating OM infections of the skin or nails. FIG. 1 shows, schematically, the preferred electrical and electromagnetic arrangement of the laser device, in which a first laser energy source 11 and a second laser energy source 12 are connected to a power source 14. The power source 14 preferably provides direct current, such as that provided by a battery, but may instead provide alternating current, such as that provided by conventional mains power, that is then converted to direct current. Switches 15, 16 are connected to the laser energy sources 11, 12 respectively and control the period of time the laser light is generated. These laser energy sources can be energized independently or simultaneously which, throughout this specification, refers to acts occurring at generally the same time.

The laser energy sources 11, 12 may be any source suitable for LLLT, including Helium-Neon lasers having a 632 nm wavelength and either solid state or tunable semiconductor laser diodes with a range of wavelengths between 400-800 nm. In the preferred embodiment, the laser energy sources 11, 12 are semiconductor laser diodes, one of which produces light in the red range of the visible spectrum, having a wavelength of about 635 nm, while the other produces light in the violet range at a wavelength of about 405 nm. Other suitable wavelengths include 440 nm, 510 nm, and 530 nm, and the wavelengths may be used in different combinations. The preferred laser energy sources 11, 12 emit less than one watt of power each. Diodes of various other wattages may also be employed to achieve the desired laser energy for the given regimen.

In the preferred embodiment, the laser light is a continuous beam. Alternatively, the laser light may be pulsed. Pulse duration controllers 21, 22 are connected to the laser energy sources 11, 12 respectively, to form a control circuit that controls the duration of each pulse of laser light emitted, referred to herein as the pulse width. Pulse widths from 0 to 100,000 Hz may be employed to achieve the desired effect on the fungus without adversely affecting the patient's tissue. The treatment goal is to deliver laser energy to the infected area utilizing a pulse width short enough to therapeutically effective against fungi while avoiding damage to adjacent tissue or laser-induced sensation in the patient's nerves.

Figure 2:
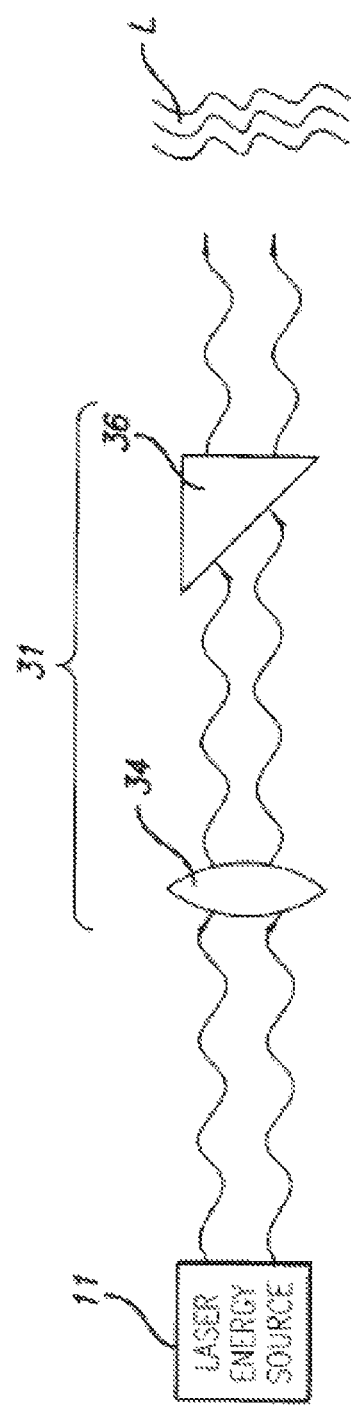
FIG. 2 is a schematic view of the optical arrangement of the linear spot shape of the preferred embodiment.

Each laser beam 41, 42 exits the corresponding laser energy source 11, 12 and is shone through optical arrangements 31, 32, respectively, that produce beam spots 1, 2 respectively of certain shapes. The beam spot is the cross-sectional shape and size of the emitted beam as it impinges the target area. For example, a laser beam of circular cross-section creates a circular beam spot as the laser light impinges the treatment area. If the laser beam is in the visible range, a circular beam spot can be seen on the treatment area of substantially the same diameter as the laser beam emitted from the laser energy source, provided the optical arrangement does not manipulate the laser beam. The laser beam can be manipulated, such as by collimation, refraction, masking, or another method of reshaping a laser beam, in order to produce beam spots of different sizes and shapes. In the preferred embodiment, the laser beams 41, 42 are shaped to produce linear beam spots on the patient. FIG. 2 illustrates an example optical arrangement 31 that includes a collimating lens 34 and a line generating prism 36. The collimating lens 34 and the line generating prism 36 are disposed in serial relation to the laser energy source 11. The collimating lens 34 and the line generating prism 36 receive and transform the generated beam of laser light into the line of laser light L. As an alternative, a suitable electrical or mechanical arrangement could be substituted for the optical arrangement 31.

Figure 3:
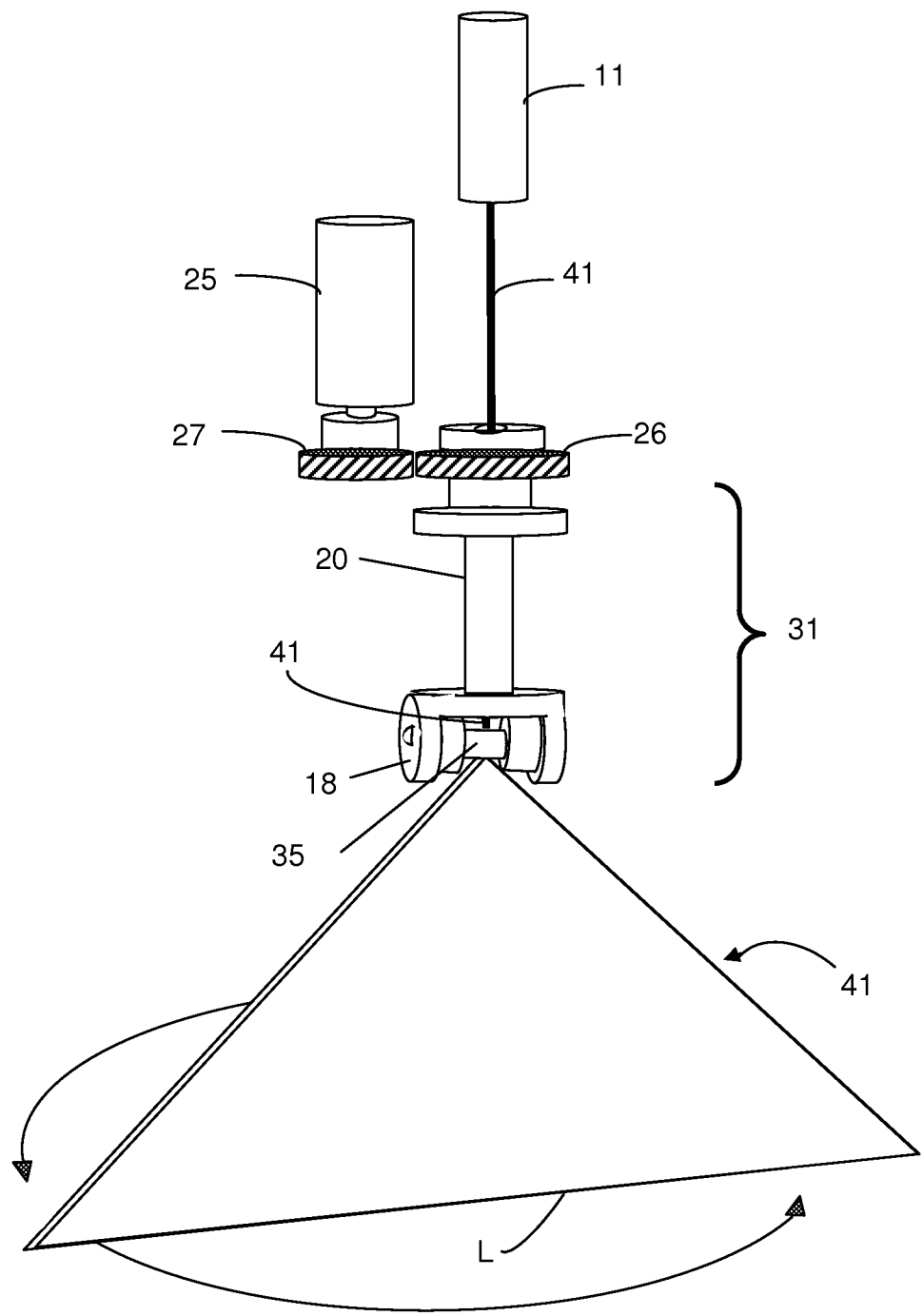
FIG. 3 is a perspective view of a scanning head optical arrangement of the present invention.
Figure 4:
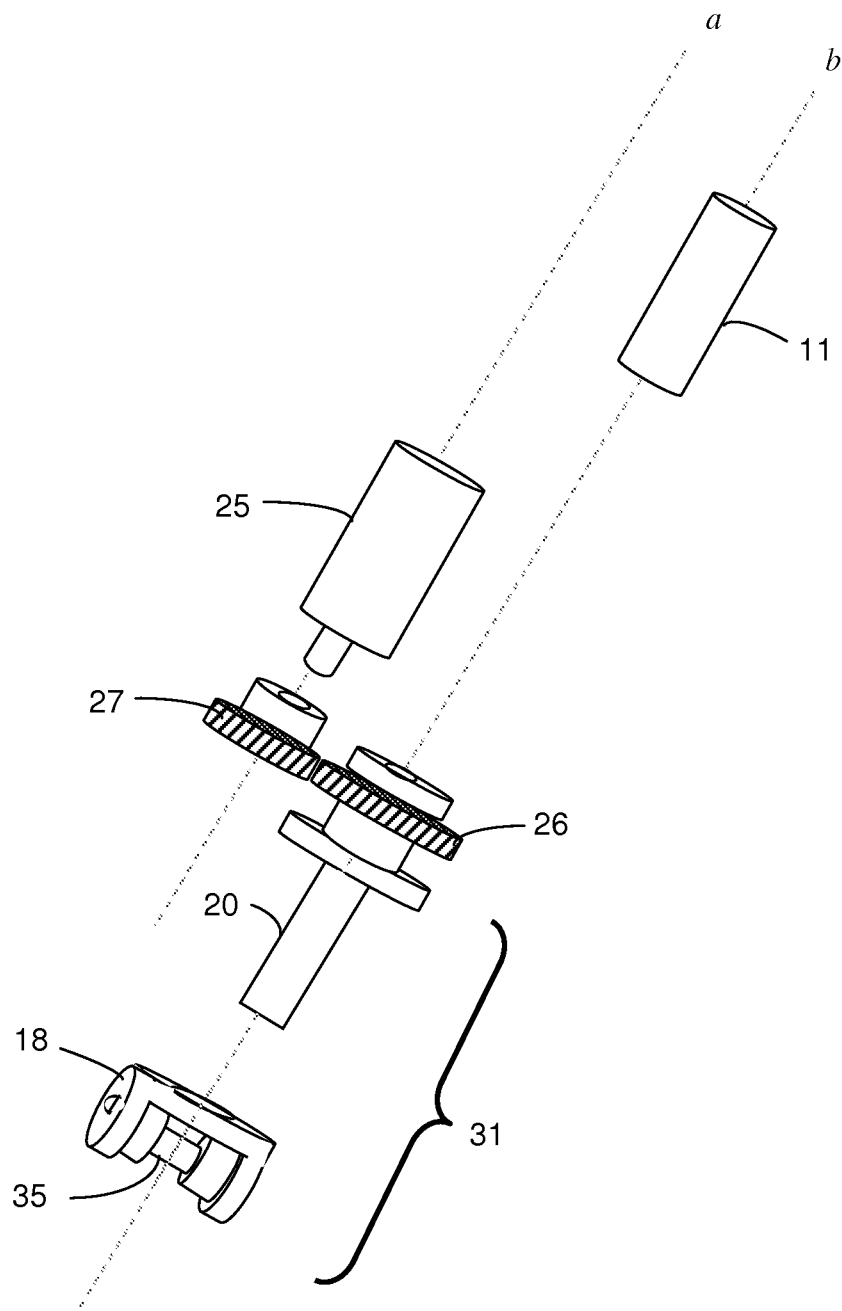
FIG. 4 is a perspective view of the scanning head of FIG. 3, exploded along axes a and b.
Figure 4A:
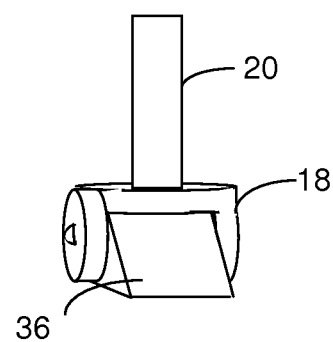
FIG. 4a is a perspective view of the universal carriage shown in FIG. 3 holding a prism instead of a rod lens.

Referring to FIGS. 3 and 4, the preferred optical arrangement 31 is a scanning head used to create a beam spot on the treatment area. To create the beam spot, the laser beam 41 emitted from the laser source 11 is directed to the scanning head, which comprises a hollow spindle 20 through which the laser beam 41 is conveyed. A rotatable carriage 18 holds an optical element upon which the laser beam 41 is incident. Preferably, the laser beam 41, spindle 20 and carriage 18 are substantially co-axial. Preferably, a linear first beam spot L with it centerpoint coaxial with the spindle 20 is generated by directing the laser beam 41 to an optical element. A rod lens 35 is preferred as the optical element, but a prism 36, as shown in FIG. 4a, or other optical element or combination thereof may suffice. In other embodiments, the first beam spot may be another circular or non-circular shape, such as a filled or outlined polygon, a multi-pointed star, or a series of parallel or crossing lines. As the carriage 18 rotates, the linear beam spot L rotates too, becoming, in essence, a rotating diameter of an apparent circular second beam spot. In the preferred embodiment, when the carriage 18 is rotated through at least 180°, the linear first beam spot L sweeps through a complete circle. Preferably, the carriage 18 is rotated slowly so that the beam spots 1, 2 impinge the same treatment area in an alternating pattern. Alternatively, with electronic or computerized control, the carriage 18 may automatically rotate very quickly, causing the laser beam 41 to appear to create a substantially circular second beam spot on the patient's skin. The shape, however, is actually the result of the scanning light diameter sweeping from location to location at a speed that makes the motion nearly imperceptible to the human eye. The longer the line, the larger the beam spot.

The carriage 18 is rotated with a drive assembly. The drive assembly is preferably a main drive gear 26 which is mated with a minor drive gear 27. The minor drive gear 27 is driven by a main drive motor 25. The carriage 18 rotates around the axis as the main drive gear 26 is turned. Thus, the laser beam 41 from laser energy source 11 passes through the hollow spindle 20 and strikes an optical element which deflects the laser beam into a linear beam spot L that, in combination with the rotation, appears as a circular beam spot. Preferably, the laser beam 41 remains coaxial with the hollow spindle 20 through the optical element, so that the center of the beam spot created by the optical element is on the axis of the hollow spindle 20. The drive assembly may also be controlled by micromanipulators according to signals received from a control pad 57, shown in FIGS. 6 and 7, which is further comprised of various discrete circuits for controlling at least the scanning head and may further control one or more of the laser energy sources, power source, switches, and pulse duration controllers, as is known in the art. In a further form, the control pad 57 includes a microprocessor programmed to operate in various modes.

Figure 5:
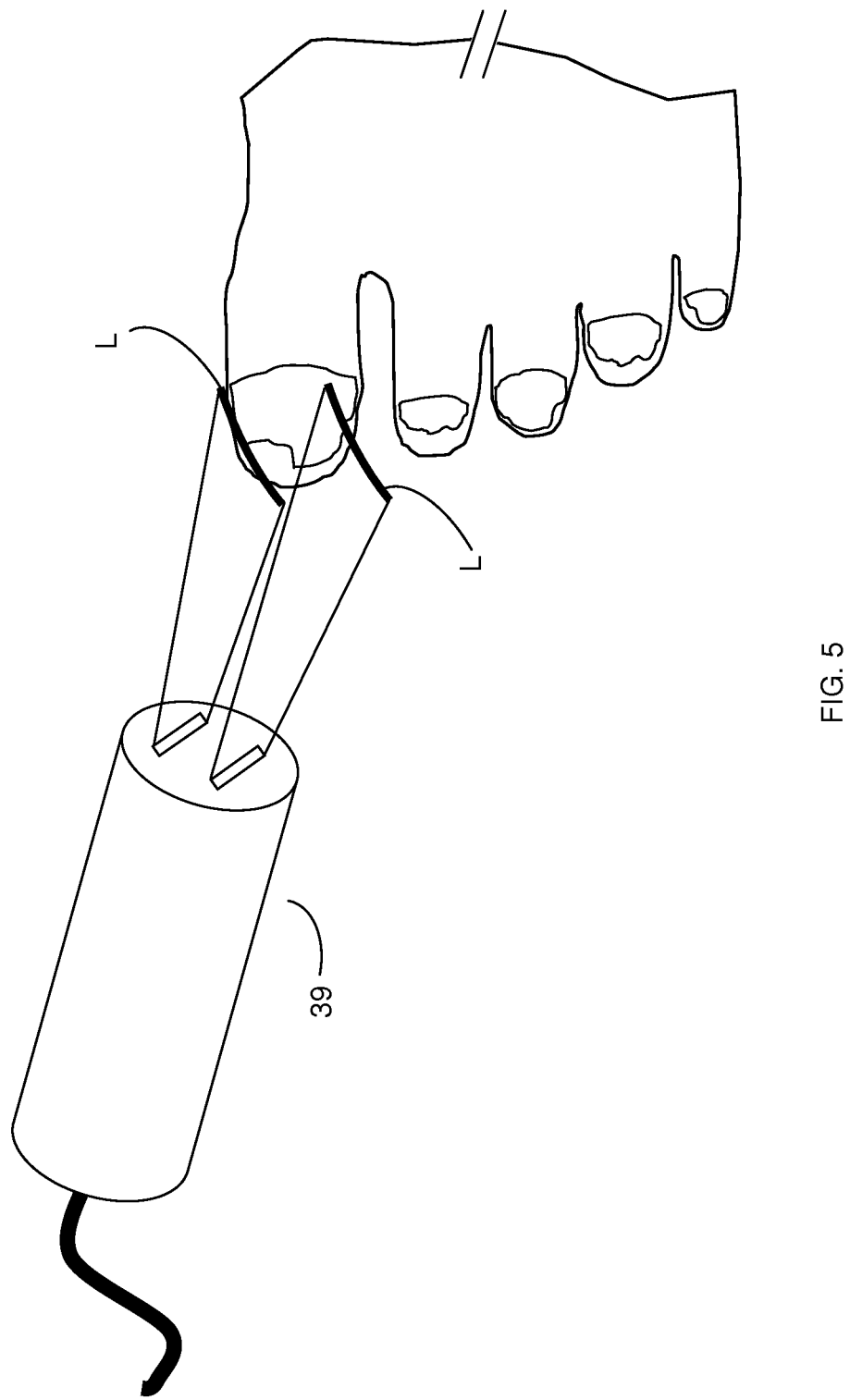
FIG. 5 is a perspective view showing application of low-level laser radiation using a hand-held wand.

Referring to FIG. 5, the laser light may be directed to the desired area on a patient using a hand-held wand 39. The wand 39 may be a housing comprising an elongated hollow tube defining an interior cavity. The laser energy source 11 and optical arrangement 31 may be mounted in the wand's 39 interior cavity, although the laser energy source could be remotely located and the laser light conducted by fiber optics to the wand 39. The wand 39 may take on any shape that enables the laser light to be directed as needed such as tubular, T-shaped, substantially spherical, or rectangular. The wand 39 may contain the power supply (for example a battery) or the power supply may be remote with power supplied by an electrical cable. As shown in FIG. 5, the laser sources 11, 12 may be mounted inside the housing of a single wand 39. Alternatively, multiple wands 39 containing one or more laser sources may be provided. If scanning heads are used as the optical arrangement 31, a scanning head may be contained wholly within each housing or attached separately to the end of each wand 39.

Figure 6:
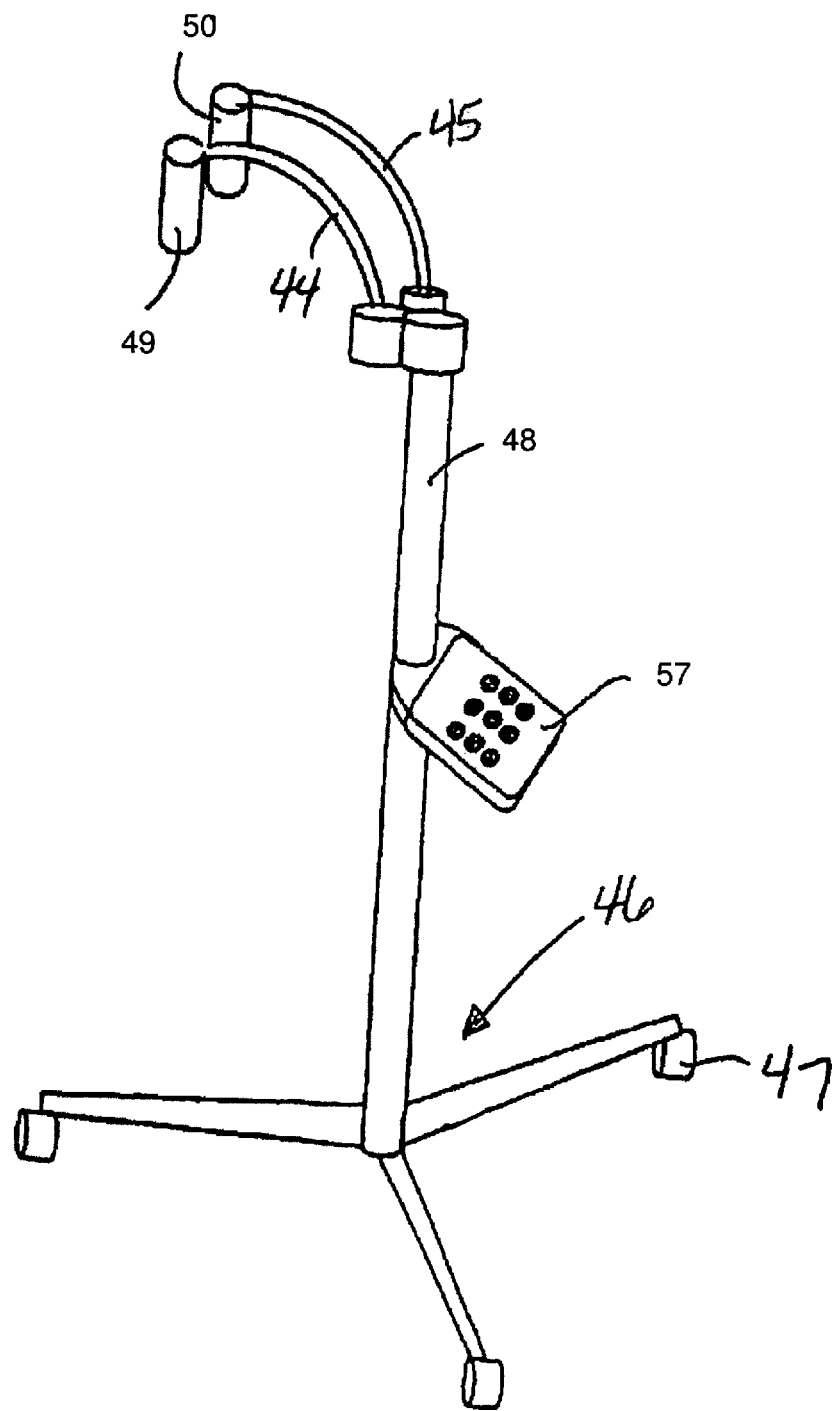
FIG. 6 is a perspective view of a portable, floor-supported laser device for use with the present invention.

Preferably, the laser device operates in a stand-alone configuration. For example, the laser device may be supported by a support structure such as the wall or a portable stand that rests on the floor or table. This stand-alone arrangement enables a patient to be scanned by the laser beam without using a handheld wand 39. Referring to FIG. 6, two housings 49, 50 are attached to an arm 48 with connectors 44, 45, respectively. It will be understood that the laser device may have a single housing or more than two housings, depending on the desired number of laser energy sources to be used. Similarly to the wand 39, each housing 49, 50 may contain one or more laser energy sources 11, 12, one or more optical arrangements 31, 32, and a power supply. The connectors 44, 45 may be rigid or, preferably, flexible, so that the housings 49, 50 can be moved to any desired position. The arm 48 may be articulated for additional control over the position of the lasers. The arm 48 is attached to a base 46 having wheels 47 such that the device can be moved to any desired position and then stay substantially stationary while treatment is occurring. This is particularly convenient for patients lying on a table or sitting in wheelchair. The control pad 57 is in electrical connection with the housings 49, 50 and may be mounted on the arm 48, in another location, or may operate as a remote control using radio frequencies or other methods known in the art.

Figure 7:
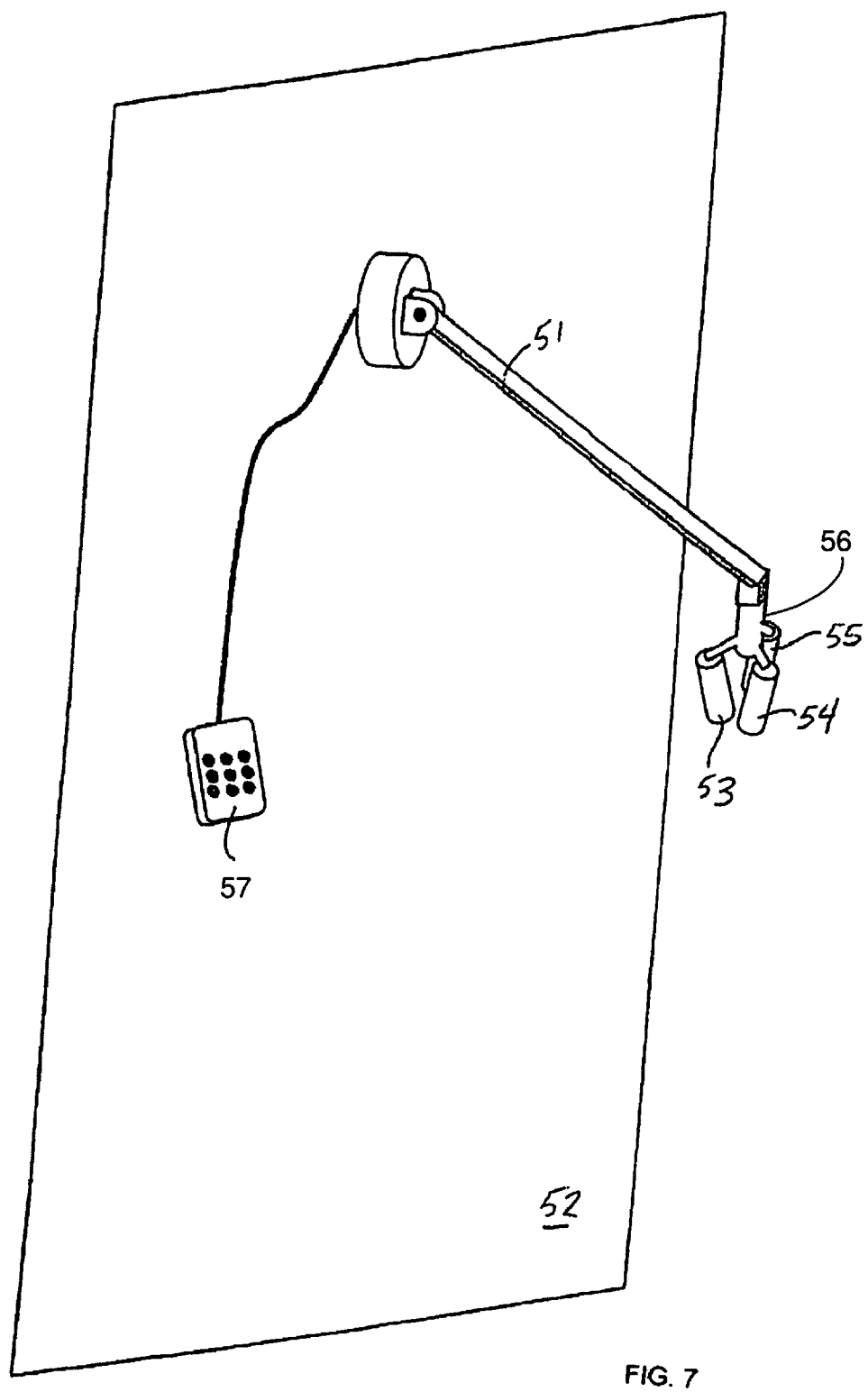
FIG. 7 is a perspective view of a wall-mounted laser device for use with the present invention.
Figure 8A:
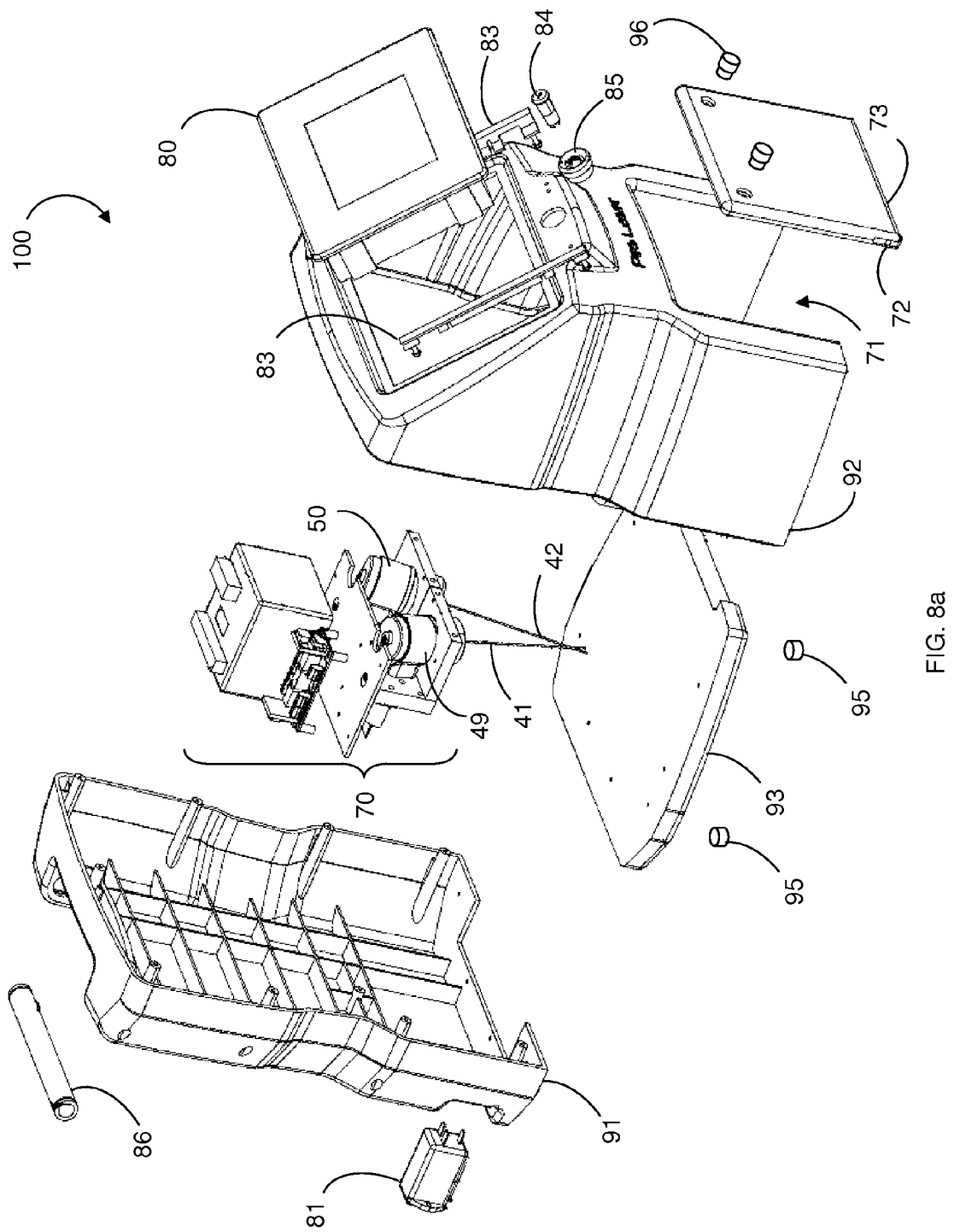
FIG. 8a is an exploded perspective view of a portable, compact, free-standing laser device for use with the present invention.
Figure 8B:
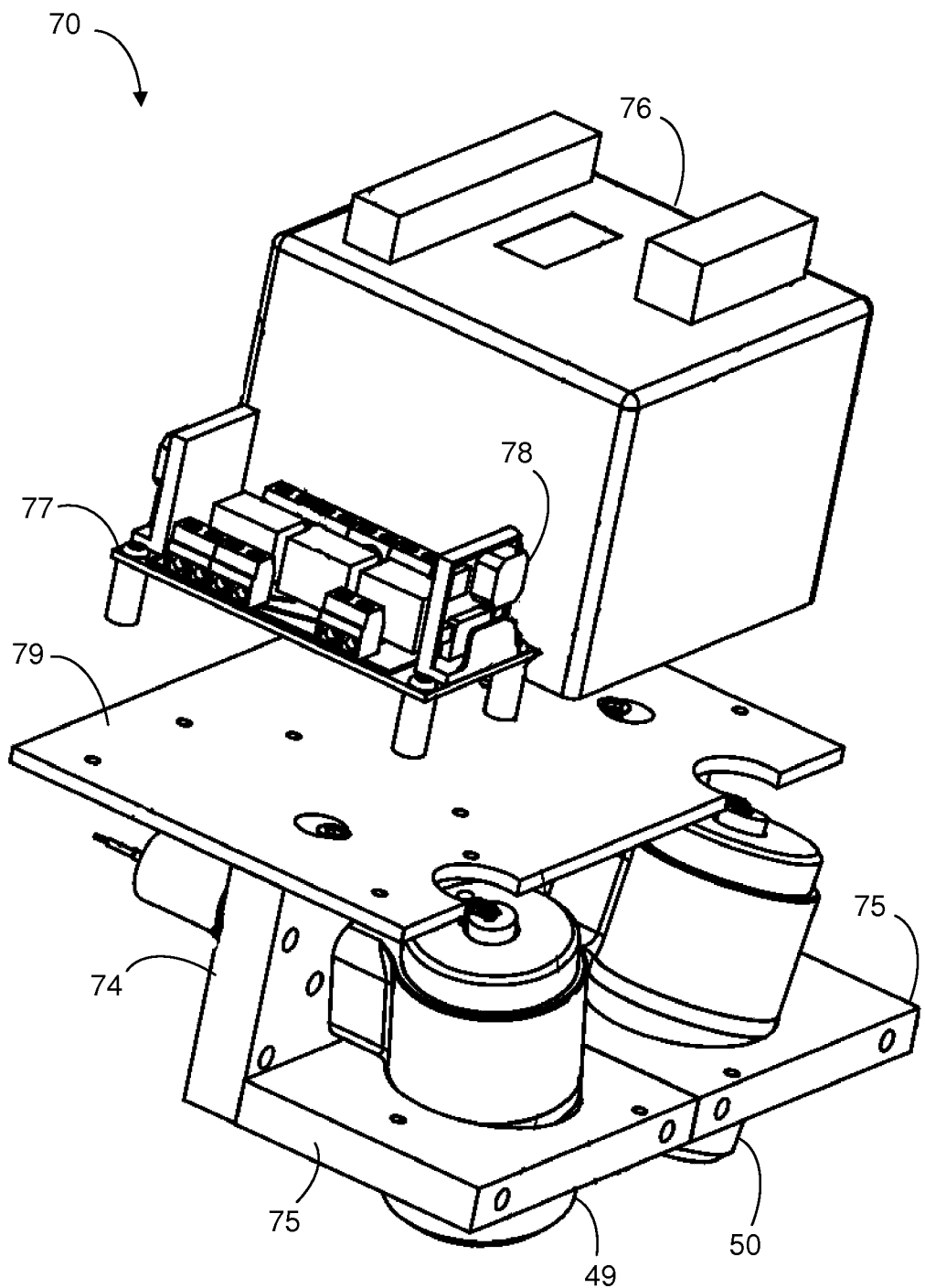
Figure 9:
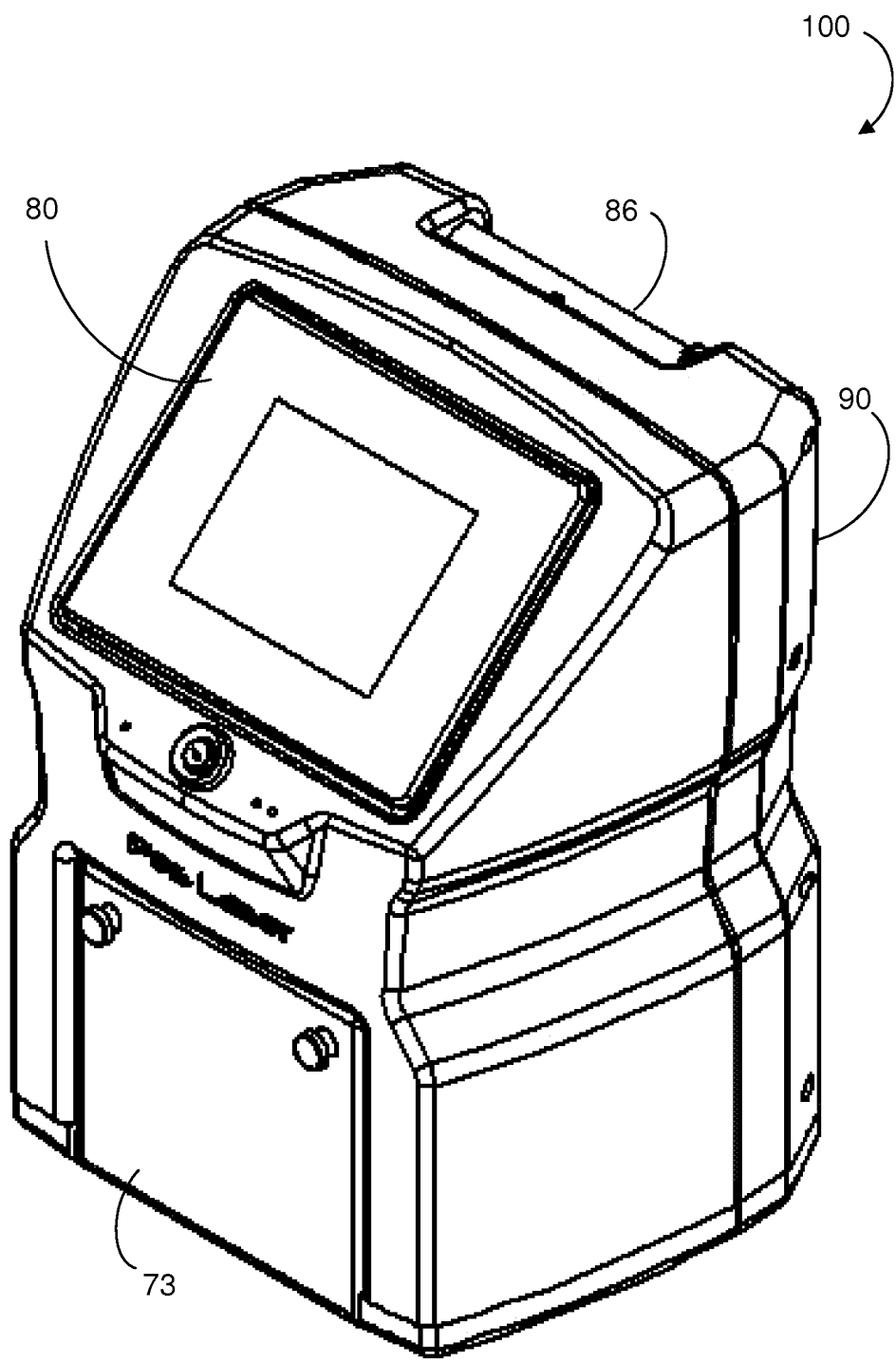
Figure 10:
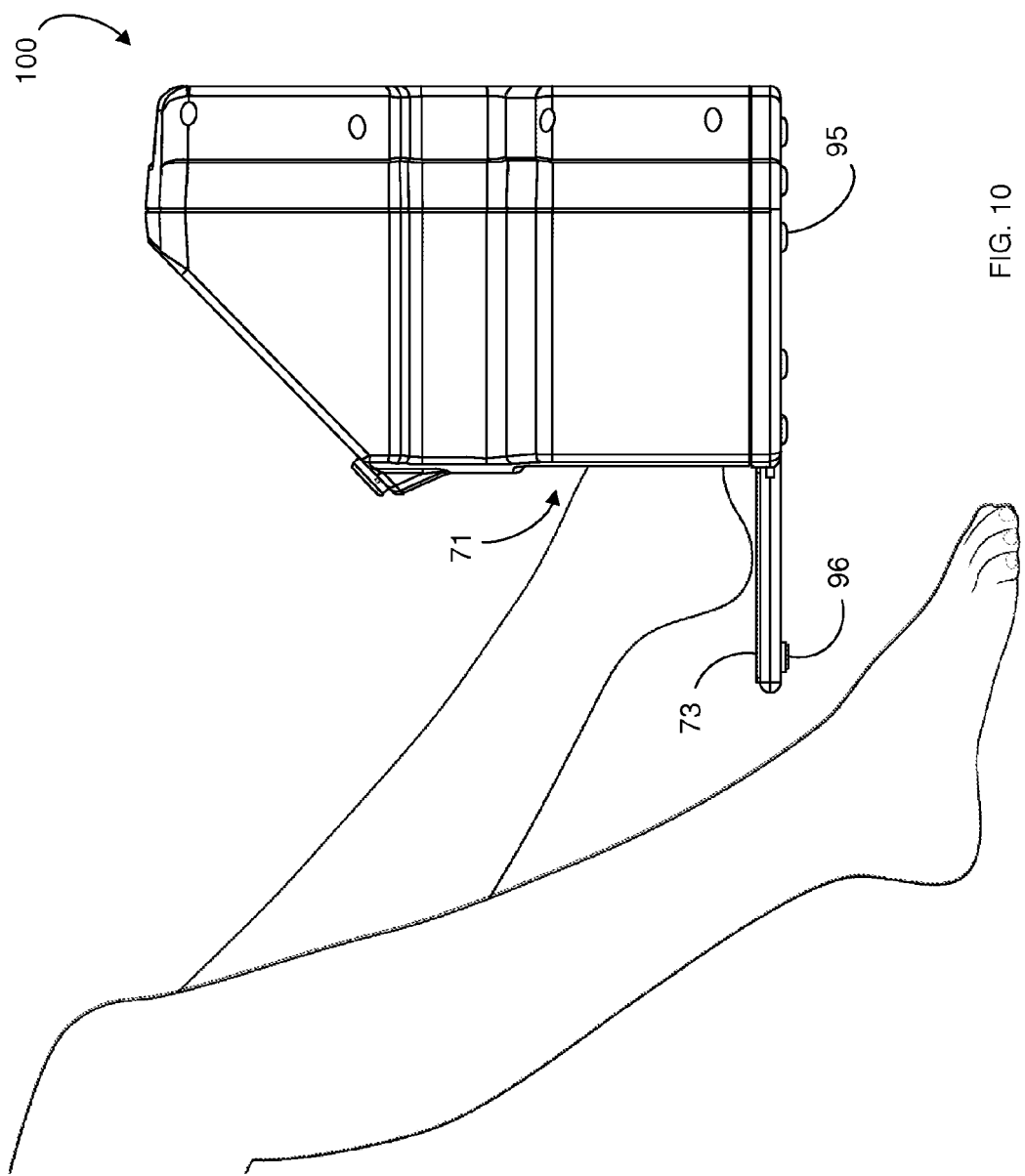
FIG. 10 is a right side view of the laser device of FIGS. 8a and 9, showing the door open and a patient's foot inserted for treatment.

Referring to FIG. 7, a three-housing assembly 56 is attached to a wall-mounted arm 51 which is affixed to the wall 52 in ways known in the art such that it can be moved to any desired position and then remain substantially stationary while therapy is occurring. The arm may be articulated for additional control over the position of the lasers. The control pad 57 is in electrical connection with the housings 53, 54, 55 and may be mounted on the wall. The control pad 57, however, can be mounted elsewhere or can operate as a remote control using radio frequencies or other methods known in the art. The assembly 56 is attached to the arm 51 in ways known in the art such that it can be moved to any desired position. Likewise, the housings 53, 54, 55 are attached to the assembly 56 so that each can be moved to a desired position.

FIGS. 8a-10 illustrate the preferred laser device 100, which is compact, portable, and free-standing. The laser device 100 is stationary during treatment, providing more uniform application of laser energy than a handheld device and occupying less space than known free-standing LLLT devices. Two housings 49, 50 are mounted in a shell 90, into which the patient places one or both feet or hands for treatment. It will be understood that, while the preferred laser device 100 includes two housings 49, 50 for emitting laser light, a similarly-functioning device may be assembled using one, three, or more housings according to the desired treatment parameters. The preferred laser device 100 preferably occupies less than two cubic feet of space. Most preferably, the shell 90 has dimensions of about 15.5 inches in height, 10 inches in width, and 10.5 inches in depth, the depth being measured from the front to the back of the shell 90. The compact size of the shell 90 allows it to be placed on a floor or countertop in a treatment room where little free space is available. Additionally, the small device 100 may be easily transported between rooms. The shell 90 comprises a back shell 91 and front shell 92 that attach to each other and to a shell base 93 to define an interior space. The back shell 91, front shell 92, and shell base 93 may made of a molded polymer, or of metal such as aluminum or steel. Preferably, the back shell 91 and front shell 92 are medical-grade polymers, while the shell base 93 is aluminum so that the laser device 100 is bottom-heavy and resistant to being knocked over. The back shell 91, front shell 92, and shell base 93 may be permanently or removably attached to each other, by adhesive or non-adhesive means. Preferably, metal or plastic screws are used to attach the back shell 91, front shell 92, and shell base 93. A handle 86 may be attached to the shell 90, preferably at the top of the back shell 91, for ease of portability. Preferably, a plurality of height-adjustable, semi-rigid feet 95 are attached to the bottom of the shell base 93. The feet 95 protect the shell base 93 from scratches and other damage, and allow the laser device 100 to be balanced on a surface that is not completely planar.

A door 73 covers an access port 71 disposed through the shell 90. The access port 71 may be in the front, back, or side of the shell 90, but preferably is disposed through the front shell 92 such that the patient's foot or hand may pass through the access port 71 into the shell 90 and rest on the shell base 93, as illustrated, for treatment. Preferably, the access port 71 is no larger than necessary to receive a substantial portion of one of the patient's feet, and is most preferably about 6.5 inches wide, about 5 inches tall, and about 8 inches deep, conforming closely to the size of the patient's hand or foot. In this manner, the shell 90 provides a substantial shield from contaminating light during the procedure; that is, the laser energy may be applied to the infected area in near darkness. The door 73 is closed when the laser device 100 is not in use, and open to allow the patient to place one or both feet or hands into the device 100. Preferably, the door 73 fits into a recess 94 in the shell base 93, so that the outer surface of the door is substantially flush with the outer surface of the front shell 92 when the door 73 is closed. The preferred door 73 then attaches to the shell base 93 with hinges 72 at the bottom of the door 73. The preferred door 73 also has one or more knobs 96 that serve a dual purpose of providing a surface to grab for opening the door 73, and contacting the surface on which the laser device 100 is placed such that the door 73 is maintained substantially parallel to the shell base 93 when open. See FIG. 10. The door 73 may then function as an extension of the top surface of the shell base 93, on which the patient's feet or hands are placed.

The housings 49, 50 are part of a scanning assembly 70 that is substantially, preferably fully, enclosed in the shell 90. Within the scanning assembly 70, a programmable logic circuit ("PLC") 76 electrically receives one or more input parameters related to the treatment to be performed. The input parameters may be received before, during, or after the treatment, and may be stored in the PLC 76 as a preset treatment. The PLC 76 uses the desired treatment parameters to control the operations of the housings 49, 50. The operations of the housings 49, 50 that may be controlled include: overall duration of laser emission from each housing 49, 50; pulse width, variation of pulse width, and duration of each pulse width application; rotational speed and direction of carriage 18, if any; and area to scan. A voltage regulator 78 manages power conversion to direct current, if needed, and regulates the voltage applied to the PLC 76, touch screen 80 and housings 49, 50. Typically, this voltage management includes reducing the voltage from mains-standard 120V or 240V to 24V for the PLC 76 and touch screen 80, and 5-8V to control the laser energy sources 11, 12 and any drive motors for rotating or oscillating optical arrangements 31, 32. The voltage regulator 78 may be a component attached to the PCB 77 as described below, or may be integrated into the PLC 76.

The housings 49, 50 are connected to a laser angle bridge 74 that sets the angle of each housing 49, 50 with respect to vertical. Preferably, the housings 49, 50 are each offset about 15 degrees from vertical so that the laser beams 41, 42 converge at a point about 5 inches below the housings 49, 50. One or more non-conductive plates 75 isolate the high-voltage components, such as the PLC 76, from the patient. The plates 75 are preferably plastic and most preferably DELRIN®. A mounting plate 79, typically made of reflective aluminum, separates the PLC 76 and the electronic components of the interface described below from the housings 49, 50, protecting the PLC 76 and the electronic components from the emitted laser light.

An interface, configured to display treatment options to a device 100 operator and receive input from the operator, may be mounted in the shell 90, in electronic communication with the scanning assembly 70. Within the interface, electronic components mounted on a printed circuit board ("PCB") 77 electrically receive input parameters. The electronic components may include transistors, resistors, capacitors, conductive traces, and other components need to form a circuit configured to receive input and transmit it to the PLC 76. An input device is electrically connected to either the PLC 76 or the components of the PCB 77, and receives the input from the operator. Preferably, the input device is attached by universal serial bus ("USB") connection to the PLC 76. The input device may be a keyboard, mouse, touch screen, microphone, or other input device. Preferably, the input device is an integrated touch screen 80 that displays options to the operator and receives the operator's selections. Preferably, the touch screen 80 is attached with interface mounts 83 installed in the front shell 92 above the door 73. Alternatively, the touch screen 80 or other combined or separate input and output devices may be remote from the shell. The touch screen 80 may receive input, which preferably comprises treatment parameters, before, after, or during treatment. The laser device 100 may require a key to be inserted before the device may be used. The allows usage to be monitored through key-checkout procedures, and also provides an emergency shutoff as required in the United States for certain alternating current-powered devices. The key is inserted into a keyswitch 84 mounted in a keyswitch mount 85 near the touch screen 80. A power module 81 connects the device to a wall outlet or alternatively may be a battery that supplies power to the device 100. The power module 81 is electrically connected to the voltage regulator 78.

In any of the disclosed laser devices, but particularly in the preferred laser device 100, parameters may be entered to program the wand 39 or any one of the housings 49, 50, 53, 54, 55 in a required manner to achieve any desired path upon the infected area of a patient. Furthermore, the device may be programmed to direct the laser output into some regions more than others so that one region may have greater treatment than another region. The scan areas of multiple optical arrangements 31, 32 may overlap, whether they emanate from the same housing or separate housings. This may be particularly useful for stand-alone apparatuses using the present invention, such as those illustrated in FIGS. 6-10. The invention is not limited to any particular programmed operation mode, but by way of example the following modes of operation are available:

1. The housing is programmed to scan the beam spot across a series of fixed regions and dwell for a pre-set period at each region. The regions may be input by a user to align with particular positions on the patient that require irradiation.
2. The carriage 18 is rotated during treatment to sweep a region of the treatment area. The rotational speed may be slow or fast, and the speed may vary during the treatment.
3. The focal position of the beam shaping elements in the optical arrangement 31, 32 is changed to generate smaller or larger spot sizes on the patient.
4. The laser power is varied.

Figure 11:
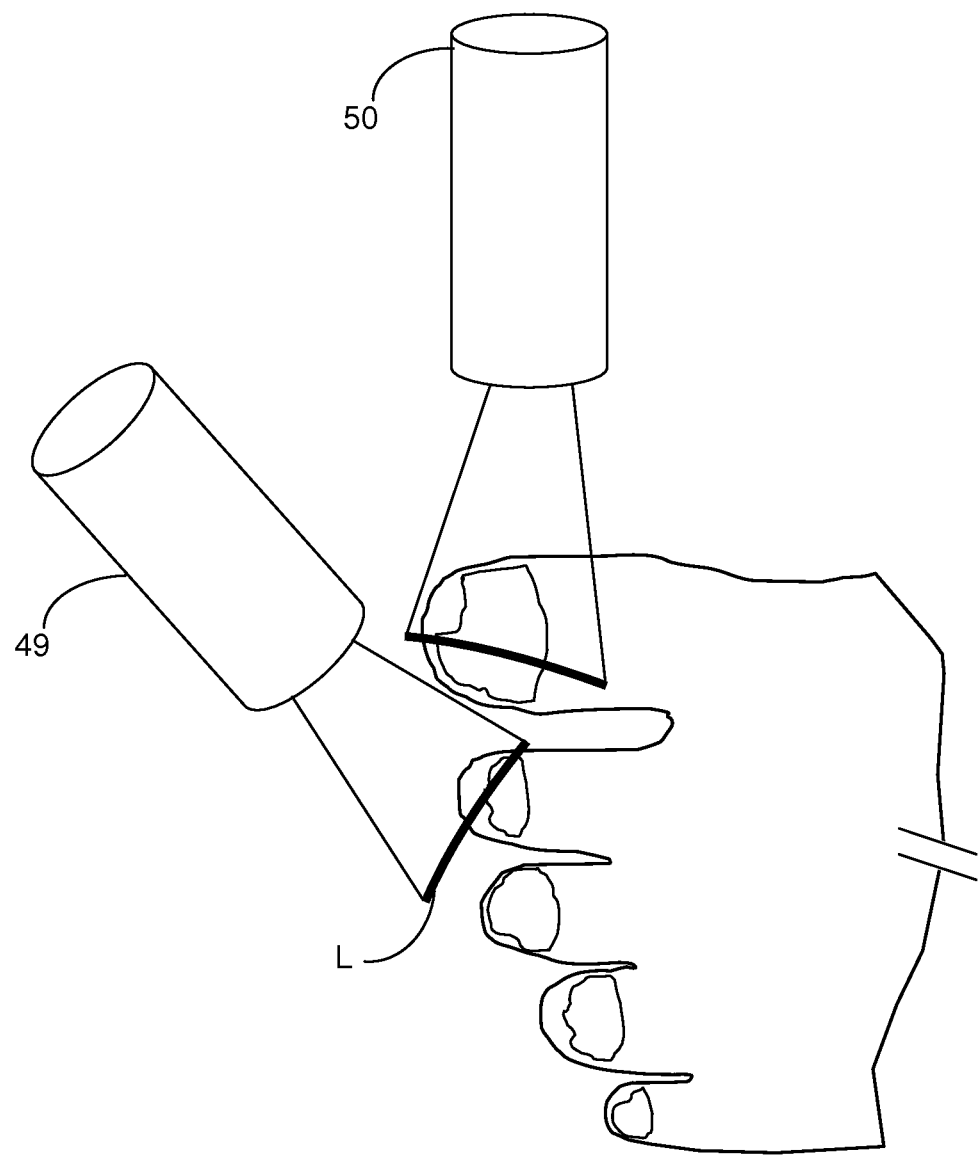
FIG. 11 is a perspective view showing application of low-level laser radiation using the laser device of FIG. 7 or 8a-10.

Preferably, including in the preferred laser device 100, the laser device employs two laser diodes each with an optical arrangement such that two substantially linear spot shapes are achieved. See FIG. 11. Further, the preferred laser device 100 has a first laser energy source 11 that emits a laser beam having a 635 nm wavelength, and a second laser energy source 12 that emits a laser beam having a 405 nm wavelength. In alternative embodiments, the device may utilize as many laser energy sources, wavelengths, and optical arrangements as necessary to obtain the desired emissions and spot shapes. For example, more than two lasers may be used and optical arrangements aligned such that two or more of the laser beams have substantially similar spot shapes and are co-incident where they impinge the patient's skin.

The disclosed laser device may, through proper application, reduce or eliminate fungi in the infected area by inciting certain processes within the fungal cells. The mitochondrial membrane of fungal cells contains cytochrome c oxidase, an identified photoacceptor molecule. Laser light from LLLT reacts with this molecule, inducing the release of highly reactive superoxides that are toxic to the fungal cell. Moreover, laser therapy has been shown to promote superoxide dismutase ("SOD"), an enzyme responsible for the destruction of pathogens, bacteria, and related foreign organisms. Extracellular release of low levels of mediators associated with SOD can increase the expression of chemokines, cytokines, and endothelial leukocyte adhesion molecules, amplifying the cascade that elicits the photodestructive response within the fungal cells.

The treatment method is performed on the patient's bare infected hands or feet. The present description uses feet and toenails to describe the method, but it will be understood that the same treatment may be used on infected hands and fingernails. The treatment is performed on each foot individually. The foot is placed flat on the floor or on a platform, with all infected nails being exposed. The laser device is positioned over the infected area. For treatments using a wand 39, the wand 39 may be positioned so that it is touching the surface of the infected nail, or it may be held at a distance of up to about 6 inches from the infected nail. For a standalone device, such as those illustrated in FIGS. 6 and 8*a*, the housings 49, 50 are preferably positioned about 4-6 inches above the infected area, most preferably about 5 inches above the infected area. In other standalone devices, the housings may be positioned about 10 inches or more from the infected surface. The device is activated and then laser light is moved slowly over the infected areas, ensuring that each receives proper photonic exposure. The laser light is preferably applied for between about 10 minutes and about 30 minutes. If both feet are infected, the treatment is repeated for the other foot.

A therapeutic amount of laser energy is applied to halt fungal cell reproduction. The appropriate therapeutic amount may depend on one or more of several factors, including: whether the infection is in the nail bed, nail plate, nail matrix, or other part of the nail; the depth and area of the infection; the density of fungal cells in the infected area; the type of fungal cells; the thickness of the nail; the concurrent use of photoreceptive topical medications, and other factors. Preferably, therefore, the extent of the infection is assessed before beginning laser energy application, so that treatment parameters may be determined. Alternatively, however, the patient may receive a dose of laser energy that is known to be generally effective for most instances of fungal infection, and the nail bed may be allowed to grow for a period of about 1-12 months to determine if the initial dose was effective. The generally-effective dose may be repeated, with or without adjusted parameters, if new nail bed growth reveals that the infection persists. Laser energy applications of about 0.5 joules per square centimeter or more may be effective, but preferably between 0.5 and 15 joules per square centimeter is applied to each foot during the treatment. The generally effective dose has approximately the following parameters: 12-minute application of laser energy, provided by a 405 nm beam and a 635 nm beam, scanned over the area such that about 10-15 joules per square centimeter total energy is applied. Typically, a single application is sufficient, but more than one application may improve the speed at which the infected nail heals. Preferably, the described application is repeated once, about five weeks after the first application. The patient may apply a photoreceptive topical medication that is activated by the laser energy and helps inhibit fungal cell reproduction. The patient may apply a topical anti-fungal medication to the infected area for 12 weeks to prevent re-infection. Successful treatment will have halted fungal cell reproduction, so that the newly-grown nail is infection free. The method results in improved nail growth rate, nail texture, and clarity, and reduced deformity.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A laser device for applying low-level laser energy to an infected area of a patient's hands or feet, the laser device comprising:
    a. a plastic shell comprising:
        i. a front shell;
        ii. a back shell removably attached to the front shell;
        iii. a shell base removably attached to the front shell and the back shell to define an interior space, the shell base comprising an edge and a recess formed into the edge; and
        iv. an access port disposed through the front shell such that the patient may insert at least one hand or at least one foot through the access port into the interior space;
    b. a scanning assembly attached to the shell and disposed in the interior space of the shell, the scanning assembly comprising:
        i. first and second housings, each housing containing:
            1. one or more laser energy sources, each having power output of less than 1 mW and configured to emit laser light having a wavelength of between 400 and 800 nm; and
            2. one or more optical arrangements, each comprising:
                a. a hollow spindle coaxial with a laser beam generated by one of the laser energy sources, and through which the laser beam is conveyed;
                b. an optical element through which the laser beam is conveyed to produce a non-circular first beam spot whose centerpoint is along the axis of the hollow spindle; and
                c. a rotatable carriage through which the laser beam is conveyed, the rotatable carriage holding the optical element;
        ii. a voltage regulator electrically attached to each of the laser energy sources, the voltage regulator configured to start, stop, and regulate power supplied to the laser energy sources;
        iii. a laser angle bridge attached to each of the first and second housings, the laser angle bridge configured to independently change the angle, with respect to the shell base, of the first and second housings;
        iv. a programmable logic circuit electrically attached to the voltage regulator and the laser angle bridge, the programmable logic circuit configured to control the voltage regulator and the operations of the first and second housings according to specified treatment parameters; and
        v. a mounting plate disposed between the housings and the programmable logic circuit;
        the scanning assembly being positioned so that the first beam spots of the first and second housings impinge on the infected area when the patient's hand or foot is in the interior space and the laser energy sources are activated;
    c. an interface electrically connected to the scanning assembly, the interface comprising:
        i. a touchscreen mounted on the front shell and configured to display treatment options and receive treatment parameters from an operator; and
        ii. a printed circuit board mounted on the mounting plate on the opposite side from the first and second housings, the printed circuit board comprising electrical components in electrical communication with the touchscreen, the electrical components forming a circuit configured to receive the treatment parameters from the touchscreen and deliver the treatment parameters to the programmable logic controller; and
    d. a door having hinges, the door being attached by the hinges to the shell base within the recess, such that the door covers the access port when closed and provides a surface on which the patient may place at least one hand or at least one foot when opened.

2. The laser device of claim 1 further comprising:

e. a plurality of feet attached to the bottom of the shell base; and f. one or more knobs attached to the door such that when the door is fully opened, the knobs contact the surface on which the laser device is placed, maintaining the open door parallel to the shell base.

3. The laser device of claim 2 further comprising a handle attached to the back shell.

* * * * *